(12) United States Patent
Krishnan et al.

(10) Patent No.: US 12,263,187 B2
(45) Date of Patent: *Apr. 1, 2025

(54) TREATMENT OF BONE MARROW PATHOLOGIES WITH POLYSULFATED POLYSACCHARIDES

(71) Applicant: PARADIGM BIOPHARMACEUTICALS LTD, Melbourne (AU)

(72) Inventors: Ravi Krishnan, Royston Park (AU); Paul Rennie, West Beach (AU)

(73) Assignee: PARADIGM BIOPHARMACEUTICALS LTD, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/116,417

(22) Filed: Mar. 2, 2023

(65) Prior Publication Data

US 2023/0241099 A1   Aug. 3, 2023

Related U.S. Application Data

(63) Continuation of application No. 16/636,545, filed as application No. PCT/AU2018/050816 on Aug. 6, 2018, now Pat. No. 11,617,763.

(30) Foreign Application Priority Data

Aug. 4, 2017   (AU) ................ 2017903094

(51) Int. Cl.
| | | |
|---|---|---|
| A61K 31/737 | (2006.01) | |
| A61K 9/00 | (2006.01) | |
| A61P 19/08 | (2006.01) | |

(52) U.S. Cl.
CPC .......... *A61K 31/737* (2013.01); *A61K 9/0019* (2013.01); *A61P 19/08* (2018.01)

(58) Field of Classification Search
None
See application file for complete search history.

(56) References Cited

U.S. PATENT DOCUMENTS

| | | |
|---|---|---|
| 9,101,650 B2 | 8/2015 | Ghosh |
| 11,617,763 B2 | 4/2023 | Krishnan et al. |
| 2014/0024614 A1 | 1/2014 | Ghosh |

FOREIGN PATENT DOCUMENTS

| | | |
|---|---|---|
| JP | 2017014204 A | 1/2017 |
| WO | 0241901 A1 | 5/2002 |
| WO | 2008144836 A1 | 12/2008 |
| WO | 2012103588 A1 | 8/2012 |
| WO | 2013055734 A1 | 4/2013 |

OTHER PUBLICATIONS

Sinusas, American Family Physician, vol. 85, No. 1, 2012. (Year: 2012).*
Notice of Allowance and Allowed Claims for AU Patent Appl. 2021201198, mailed Jun. 22, 2022.
Osteoarthritis, Treatment & management—Australian Institute of Health and Welfare, https://www.aihw.gov.au/reports/chronic-musculoskeletal-conditions/osteoarthritis/contents/treatment-management, accessed Jan. 9, 2022.
Altahawi, F.F. et al., "Comparing an accelerated 3D fast spin-echo sequence (CS-SPACE) for knee 3-T magnetic resonance imaging with traditional 3D fast spin-echo (SPACE) and routine 2D sequences", Skeletal radiology; 46(1), 2016, 7-15.
Anderson, V.R. et al., "Pentosan polysulfate: a review of its use in the relief of bladder pain or discomfort in interstitial cystitis", Drugs; 66(6), 2006, 821-835.
Batemen, D. et al., "Non-steroidal anti-inflammatory drugs and elderly patients", British Medical Journal; 310, 1995, 817-818.
Boks, S.S. et al., "Clinical consequences of posttraumatic bone bruise in the knee", Am J Sports Med 2007; 35(6), 2007, 990-995.
Bonnin, M. et al., "Osteoarthritis of the Knee", Springer-Verlag, France, 2008, 635 pages.
Brandt, K.D., "Should nonsteroidal anti-inflammatory drugs be used to treat osteoarthritis?", Rheumatic Disease Clinics of North America; 19, 1993, 29-44.
Briggs, K.K. et al., "Reliability, validity, and responsiveness of the Lysholm knee score and Tegner activity scale for patients with meniscal injury of the knee", The Journal of bone and joint surgery American vol. 88(4), 2006, 698-705.
Chaler, J. et al., "Painful lateral knee condyle bone marrow edema after treatment with lateral wedged insole", Am J Phys Med Rehabil; 89(5), 2010, 429-433.
Davies, N.H. et al., "Magnetic resonance imaging of bone bruising in the acutely injured knee-short-term outcome", Clin Radiol; 59(5), 2004, 439-445.
Davies-Tuck, M.L., "The natural history of bone marrow lesions in community-based adults with no clinical knee osteoarthritis", Annals of the Rheumatic Diseases.; 68(6), 2009, 904-908.
Davis, E.L. et al., "Safety and efficacy of the use of intravesical and oral pentosan polysulfate sodium for interstitial cystitis: a randomized double-blind clinical trial", J Urol; 179(1), 2008, 177-185.
Dimitrakov, J. et al., "Pharmacologic management of painful bladder syndrome/interstitial cystitis: a systematic review", Arch Intern Med; 167(18), 2007, 1922-1929.
Eriksen, E.F., "Treatment of bone marrow lesions (bone marrow edema)", BoneKey Reports 4, Article No. 755, 2015.

(Continued)

*Primary Examiner* — Layla D Berry
(74) *Attorney, Agent, or Firm* — Dorsey & Whitney LLP

(57) ABSTRACT

The present invention relates to the medical use of polysulfated polysaccharides and compositions thereof for the treatment of disease or disorders associated with bone marrow pathologies in the musculoskeletal system of a mammal. In particular, the invention relates to use of polysulfated polysaccharides, such as pentosan polysulfate, in treatment of bone marrow edema lesions or spinal Modic Endplate Changes as assessed by magnetic resonance imaging (MRI).

13 Claims, 2 Drawing Sheets

(56) References Cited

OTHER PUBLICATIONS

Fairbank, J.C.T. et al., "The Owestery Disability Index", Spine, 25(22), 2000, 2940-2953.

Fatiadou, A., "Wrist injuries in young adults: The diagnostic impact of CT and MRI", Eur J Radiol., Jun. 14, 2010.

Felson, D.T., "Bone marrow edema and its relation to progression of knee osteoarthritis", Annals of internal medicine;139(5 Pt 1), 2003, 330-336.

Felson, D.T. et al., "The association of bone marrow lesions with pain in knee osteoarthritis", Annals of internal medicine;134(7), 2001, 541-549.

Ghosh, P. et al., "Effects of pentosan polysulfate in osteoarthritis of the knee: a randomized, double-blind, placebo-controlled pilot study", Current Ther Research; 6, 2005, 552-571.

Ghosh, P., "The pathobiology of osteoarthritis and the rationale for the use of pentosan polysulfate for its treatment", Sem Arthritis Rheum; 28, 1999, 211-267.

Gonc, U. et al., "Bone bruises of the knee", Acta Orthop Traumatol Turc; 41 Suppl 2, 2007, 98-104.

Hayashi, D. et al., "Semiquantitative assessment of subchondral bone marrow edema-like lesions and subchondral cysts of the knee at 3T MRI: A comparison between intermediate-weighted fatsuppressed spin echo and Dual Echo Steady State sequences", BMC Musculoskeletal Disorders; 12, 2011, 198-206.

Hjermstad, M.J. et al., "Studies comparing Numerical Rating Scales, Verbal Rating Scales, and Visual Analogue Scales for assessment of pain intensity in adults: a systematic literature review", Journal of pain and symptom management; 41(6), 2011, 1073-1093.

Hoffman, S. et al., "The painful bone marrow edema syndrome of the hip joint", Wien Klin Wochenschr; 117(4), 2005, 111-120.

Hofmann, S. et al., "Painful bone marrow edema of the knee: differential diagnosis and therapeutic concepts", Orthop. Clin. N. Am., 35, 2004, 321-333.

Hunter, et al., "The reliability of a new scoring system for knee osteoarthritis MRI and the validity of bone marrow lesion assessment: BLOKS (Boston Leeds Osteoarthritis Knee Score)", Ann. Rheum. Dis, 67, 2008, 206-211.

Hunter, D.J. et al., "Increase in bone marrow lesions associated with cartilage loss: a longitudinal magnetic resonance imaging study of knee osteoarthritis", Arthritis and rheumatism; 54(5), 2006, 1529-1535.

Huskisson, E.C., "Effects of anti-inflammatory drugs on the progression of osteoarthritis of the knee", Journal of Rheumatology; 22, 1995, 1941-1946.

Koo H-K, H-K et al., "Bone Marrow Edema and associated pain in early stage osteonecrosis of the femoral head: prospective study with serial MR images", Radiology; 213, 1999, 715-722.

Kream, B., "Clinical and basic aspects of glucocorticord actions in bone", Principle of Bone Biology vol. 1 Chapter 44; Eds: Bilezikian, Raisz LG, Roe GA. Elsevier B V Netherlands Academic Press New York, 2008.

Krupinski, K. et al., "Anticoagulant and antithrombotic effects of chemically modified heparins and pentosan polysulfate", Haemostasis; 20(2), 1990, 81-92.

Kumagai, K. et al., "Sodium pentosan polysulfate resulted in cartilage improvement in knee osteoarthritis—an open clinical trial", BMC Clin Pharm; 10, 2010, 1-9.

Kuttapitiya, et al., "Microarray analysis of bone marrow lesions in osteoarthritis demonstrates upregulation of genes implicated in osteochondral turnover, neurogenesis and inflammation", Ann. Rheum. Dis., Oct. 2017;76(10):1764-1773, 10 pages.

Laslett, L.L. et al., "Zoledronic acid reduces knee pain and bone marrow lesions over 1 year: a randomised controlled trial", Ann Rheum Dis.; 71(8), 2012, 1322-1328.

Losonczy, H., "Effect of pentosan polysulfate on activated partial thromboplastin time, thrombin time, euglobulin clot lysis and tissue-type plasminogen activator and plasminogen activator inhibitor activities in patients with thromboembolic disease", Semin Thromb Hemost; 17(4), 1991, 394-398.

Lovell, G. et al., "Osteitis pubis and assessment of bone marrow edema at the pubic synphysis with MRI in an elite junior male soccer squad", Clin J Sport Med; 16(2), 2006, 117-122.

Lowitz, T., "Bone marrow lesions identified by MRI in knee osteoarthritis are associated with locally increased bone mineral density measured by QCT", Osteoarthritis and cartilage.; 21(7), 2013, 957-964.

Masala, Salvatore et al., "Treatment of painful Modic type I changes by vertebral augmentation with bioactive resorbable bone cement", Neuroradiology 56, 2014, pp. 637-645.

Mayerhoefer, M.E. et al., "Short-term outcome of painful bone marrow oedema of the knee following oral treatment with iloprost or tramadol: results of an exploratory phase II study of 41 patients", Rheumatology; 46(9), 2007, 1460-1465.

Mckenzie, L.S. et al., "Effect of anti-inflammatory drugs on sulphated glycosaminoglycan synthesis in aged human articular cartilage", Ann rheum Dis; 35(6), 1976, 487-497.

Miyata, N. et al., "Pentosan reduces osteonecrosis of femoral head in SHRSP", Clinical and experimental hypertension (New York, NY : 1993); 32(8), 2010, 511-516.

Nakame, A. et al., "Natural history of bone bruises after acute knee injury: clinical outcome and histopathological findings", Knee Surg Sports Traumatal Arthrose; 14, 2006, 1252-1258.

O'Loughlin, PF et al., "Current concepts in the diagnosis and treatment of osteochondral lesions of the ankle", Am J Sports Med; 38, 2010, 392-404.

O'Mahony, D. , "Prevention of corticosteroid-induced osteoporosis and fractures", Journal of Clinical Pharmacy and Therapeutics; 24(2), 1999, 83-85.

Omar, I.M. et al., "Athletic pubalgia and "sports hernia": optimal MR imaging technique and findings", Radiographies; 28(5), 2008, 1415-1438.

Orchard, J. et al., Injury Report—Australian Football League; Wednesday May 12, 2010., 2009.

Orr, JD et al., "Painful bone marrow edema syndrome of the foot and ankle", Foot Ankle Int; 31(11), 2010, 949-953.

International Search Report and Written Opinion, App. No. PCT/AU2018/050816, Sep. 5, 2018, 13 pages.

Powell, S.E. et al., "Standing magnetic resonance imaging detection bone marrow oedema-type signal pattern associated with subcarpal pain in 8 racehorses: a prospective study", Equine Vet J; 42(1), 2010, 10-17.

Radin, E.I., "The importance of bone in sparing articular cartilage from impact", Clin Orthop Related Res.; 78, 1971, 342-344.

Radin, E.R., "The pathogenesis of primary osteoarthritis", Lancet, Jun. 24, 1972, 1395-1396.

Rahme, R. et al., "The modic vertebral endplate and marrow changes: pathologic significance and relation to low back pain and segmental instability of the lumbar spine", AJNR Am J Neuroradiol.; 29(5), May 2008, 838-842.

Raynauld, J.P. et al., "Correlation between bone lesion changes and cartilage volume loss in patients with osteoarthritis of the knee as assessed by quantitative magnetic resonance imaging over a 24-month period", Ann Rheum Dis.; 67(5), 2008, 683-688.

Roemer, F.W., "Change in MRI-detected subchondral bone marrow lesions is associated with cartilage loss: the MOST Study. A longitudinal multicentre study of knee osteoarthritis", Ann Rheum Dis.; 68(9), 2009, 1461-1465.

Romas, E., "Corticosteroid-induced osteoporosis and fractures", Australian Prescriber; 31(2), 2008, 45-49.

Roos, E.M. et al., "Knee injury and Osteoarthritis Outcome Score (KOOS): from joint injury to osteoarthritis", Health Qual Life Outcomes; 1:64, 2003.

Sampson, Matthew J. et al., "Improved clinical outcome measures of knee pain and function with concurrent resolution of subchondral Bone Marrow Edema Lesion and joint effusion in an osteoarthritic patient following Pentosan Polysulphate Sodium treatment: a case report", BMC Musculoskeletal Disorders 18:396, 2017, 5 pages.

Scully, M.F. et al., "Anticoagulant and antiheparin activities of a pentosan polysulphate", Thrombosis Research; 31(1), 1983, 89-97.

Shanmugam, M. et al., "Heparinoid-active sulphated polysaccharides from marine algae as potential blood anticoagulant agents", Current Science; 79(12), 2000, 1672-1683.

(56) References Cited

OTHER PUBLICATIONS

Starr, A.M. et al., "Bone marrow edema: pathophysiology, differential diagnosis, and imaging", Acta radiologica (Stockholm, Sweden: 1987); 49(7), 2008, 771-786.

Szkopek, K. et al., "Pain and Knee function in relation to degree of bone bruise after acute anterior cruciate ligament rupture", Scand J Med Sci Sports, doi: 10.1111/j.1600-0838.2011.01297.x. [Epub ahead of print], Apr. 8, 2011.

Tanamas, S.K., "Bone marrow lesions in people with knee osteoarthritis predict progression of disease and joint replacement: a longitudinal study", Rheumatology (Oxford, England); 49(12), 2010, 2413-2419.

Tanamas, S.K. et al., "The association between subchondral bone cysts and tibial cartilage volume and risk of joint replacement in people with knee osteoarthritis: a longitudinal study", Arthritis Research and Therapy; 12:R58, 2010.

Theologis, A. A. et al., "Evaluation of bone bruises and associated cartilage in anterior cruciat ligament injured and—reconstructed knees using quantitative 1 tesla magnetic resonance imaging", 1-year cohort study. Arthroscopy; 27(1), 2011, 65-76.

Thiryayi, WA, "Histopathological perspective on bone marrow oedema reactive bone change and haemorrhage", Eur J Radiol; 67(1), 2008, 62-67.

Unay, K. et al., "The relationship between bone marrow edema size and knee pain", Knee Surg Sports Traumatol Arthrosc; 17(11), 2009, 1298-1304.

Varenna, M. et al., "Intravenous neridronate in the treatment of acute painful knee osteoarthritis: a randomized controlled study", Rheumatology (Oxford, England).; 54(10), 2015, 1826-1832.

Verrall, GM et al., "Incidence of pubic bone marrow oedema in Australian Rules football players: relation to groin pain", Br J Sports Med; 35, 2001, 28-33.

Vinazzer, H., "Prevention of recurrence of cerebrovascular thromboses. A randomized comparative study acetylsalicylic acid and sodium pentosan polysulfate", Fortschr Med; 105(5), 1987, 79-85.

Vongchan, P. et al., "Anticoagulant activities of the chitosan polysulfate synthesized from marine crab shell by semi-heterogeneous conditions", Science Asia; 29, 2003, 115-120.

Voormolen, MHJ et al., "Bone marrow edema in osteoporotic vertebral compression fractures after percutaneous vertebroplasty and relation with clinical outcome", American J Neuroradiology; 27, 2006, 983-988.

Werb, Z., "Biochemical actions of glycocorticoids on macrophages in culture. Specific in activator secretion and effects on other metabolic functions", JEM; 147(6), 1978, 1695-1712.

Wikipedia, "Modic changes", https://en.wikipedia.org/wiki/Modic_changes (Accessed Feb. 6, 2020), Jul. 21, 2017, 3 pages.

Wilkens, Philip et al., "No effect of 6-month intake of glucosamine sulfate on Modic changes or high intensity zones in the lumbar spine: sub-group analysis of a randomized controlled trial", Journal of Negative Results in BioMedicine 11:13, 2012, 10 pages.

Wluka, A.E. et al., "Bone marrow lesions predict increase in knee cartilage defects and loss of cartilage volume in middle-aged women without knee pain over 2 years", Ann Rheum Dis; 68, 2009, 850-855.

Wluka, A.E. et al., "Bone marrow lesions predict progression of cartilage defects and loss of cartilage volume in healthy middle-aged adults without knee pain over 2 yrs", Rheumatology (Oxford, England);47(9), 2008, 1392-1396.

Zhai, G. et al., "Correlates of knee pain in older adults: Tasmanian Older Adult Cohort Study", Arthritis and rheumatism; 55(2), 2006, 264-271.

Kellgren-Lawrence Scale for radiographic classification of osteoarthritis—McMaster Textbook of Internal Medicine Table 18.13-1, https://empendium.com/mcmtextbook/table/031_0728; accessed Aug. 21, 2022.

Numeric Rating Scale (NRS), National Center for Biotechnology Information, U.S. National Library of Medicine, Medscape, National Center for Biotechnology Information, U.S. National Library of Medicine, www.painscale.com/article/numeric-rating-scale-nrs, 2 pages, dated Oct. 21, 2024.

Jensen, Mark P., et al., Jensen et al., Interpretation of Visual Analog Scale Ratings and Change Scores: A Reanalysis of Two Clinical Trials of Postoperative Pain, The Journal of Pain, vol. 4, No. 7 Sep. 2003: pp. 407-414.

* cited by examiner

Pre-treatment

Post-treatment

TREATMENT OF BONE MARROW PATHOLOGIES WITH POLYSULFATED POLYSACCHARIDES

CROSS REFERENCE TO RELATED APPLICATIONS

This application is a continuation of U.S. patent application Ser. No. 16/636,545 filed Feb. 4, 2020, entitled "TREATMENT OF BONE MARROW PATHOLOGIES WITH POLYSUFATED POLYSACCHARIDES", which is a national stage application under 35 U.S.C. § 371 of International Application No. PCT/AU2018/050816 filed Aug. 6, 2018, entitled "TREATMENT OF BONE MARROW PATHOLOGIES WITH POLYSULFATED POLYSACCHARIDES" which claims priority to Australian Patent Application No. 2017903094 filed Aug. 4, 2017, the contents of each of which is hereby incorporated herein in their entirety by reference.

TECHNICAL FIELD

This invention relates to the medical use of polysulfated polysaccharides and compositions thereof for the treatment of disease or disorders associated with bone marrow pathologies in the musculoskeletal system of a mammal. In particular, the invention relates to use of polysulfated polysaccharides in treatment of bone marrow edema lesions or spinal Modic Endplate Changes as assessed by magnetic resonance imaging (MRI).

BACKGROUND

Bone Marrow Edema Lesions

Bone marrow edema lesions (BMEL) are changes that occur in the subchondral bone and are detected by MRI depicting the severity of symptoms including pain ([1]-[3]) and cartilage degeneration ([4]-[7]) in osteoarthritic patients. BMELs are generally evaluated using fat-suppressed proton density or T2-weighted sequences. In fat suppressed T2-weighted and fat suppressed proton density weighted sequences BMELs appear as hyper-intense signals [8].

The MRI signals related to the BMELs are thought to arise from an increase in concentration of blood and interstitial fluids (including infiltrating macrophages) in areas of trabecular microfractures and collapse within the bone marrow [8]. Improved spatial resolution and multiplanar reconstructions provide a potential role of 3D fast spin echo sequences, particularly for imaging of cartilage [9].

There are increasing data that suggest that BMELs play an important role in the pathogenesis of arthritic conditions such as osteoarthritis conditions which include knee osteoarthritis.

Knee Osteoarthritis

Knee osteoarthritis (OA) is a disorder characterized by bone changes around the knee joint, progressive loss of joint cartilage, joint space narrowing, and eventual total joint failure. Knee OA results in knee pain, significant physical disability, and reduced quality of life. Results of epidemiological studies suggest that there are approximately 12 million patients in the United States, 50 years of age and older, with symptomatic knee OA, of whom an estimated approximately 7 million have BMLs.

Patients with knee osteoarthritis may exhibit BMELs that appear as areas of increased signal intensity on MRI of the knee, and in established disease BMELs are associated with knee pain [2], disease severity and disease progression including radiological progression of knee osteoarthritis [10] and cartilage loss based on MRI ([5], [11]). Furthermore, in progressive osteoarthritis BMELs are more likely to persist and enlarge in size with an associated increase in cartilage loss [5]. Moreover, the severity of BMEL has been shown to correlate with the risk of knee arthroplasty [12].

The strong association with BMEL with pain and loss of cartilage has heightened pharmaceutical interest to target this structural lesion for monitoring progression of knee osteoarthritis and therapeutic effects ([13]-[15]).

Chronic Low Back Pain

Chronic Low Back Pain (CLBP) is defined as persistent or fluctuating low back pain lasting at least three months. CLBP, or back pain in general, is a disabling and costly condition that is associated with increased healthcare utilization. Some patients with CLBP exhibit Modic changes (MCs) which are vertebral bone marrow changes that are visible on MRI of the spine.

Of the three classified MCs, Type I, II and III, Type I changes are hypointense on T1-weighted imaging (T1WI) and hyperintense on T2-weighted imaging (T2WI) and represent bone marrow edema and inflammation. Type II changes are hyperintense on T1WI and isointense or slightly hyperintense on T2WI and were associated with conversion of normal red hemopoietic bone marrow into yellow fatty marrow as a result of marrow ischemia. Modic Type III changes are described as hypointense on both T1WI and T2WI and were thought to represent subchondral bone sclerosis. Mixed-type I/II and II/III Modic changes have also been reported, suggesting that these changes can convert from one type to another [15A].

Of the three classified MCs, Type I, II and III, Type I are especially associated with low back pain, persistent symptoms and poor outcomes. Results of epidemiological studies suggest that there are approximately 9 million adults in the United States with CLBP, of whom an estimated approximately 1.6 million have type I MCs.

The economic costs of CLBP are estimated to range from $12.2 billion to $90.6 billion annually in the United States. Factors that contribute to this economic impact include prolonged loss of function, consequent loss of work productivity, treatment costs, and disability payments.

Patients with CLBP may exhibit MCs. MCs are vertebral bone marrow changes that are visible on MRI of the spine, and that are associated with low back pain, based on published studies. Findings from various studies have demonstrated that the presence of MCs, especially type I MCs, is correlated with low back pain, predicts persistent symptoms, and sick leaves, and is associated with poor outcomes. These findings suggest that MCs are a potential target for pharmaceutical intervention.

Polysulfated Polysaccharides

Heparin and structurally related polysulfated polysaccharides such as pentosan polysulfate, chitosan polysulfate, the fucans etc have been used for a number of years as anticoagulants [16-21]. Pentosan polysulfate (PPS) is a weaker anticoagulant than heparin [16, 18, 20] but has been used post-surgically and prophylactically as a thrombolytic agent [21]. When given via the oral and intrathecal routes, PPS has been used for the treatment of interstitial cystitis (inflammation of the bladder) [22-24]. Indeed, PPS is the active agent in the drug ELMIRON® which is currently prescribed for interstitial cystitis. The potential use of PPS in treatment of inflammatory conditions such as asthma, allergic rhinitis, and/or chronic obstructive pulmonary disease (COPD) has also been described [25], as has the use of PPS in osteoporosis [26]; and the use of PPS in bone marrow edema [27].

Current treatment options for BMELs are diverse with limited reports of improved clinical outcome. The standard treatment of BMELs in osteoarthritic patients consists of analgesic or anti-inflammatory medications combined with reduced weight-bearing and physical therapy until symptoms disappear [28]. However, non-steroidal antiinflammatory drugs (NSAIDs) and corticosteroids have been found to have negative effects on bone healing and the metabolism of cartilage ([29]-[32]). The risk of fracture, both traumatic and spontaneous, is increased in those subjects that take continuous corticosteroid therapy [31]. There is a need for pharmaceuticals that do not have these negative effects in expanding the repertoire of pharmaceutical agents available in providing new and improved medicines for bone marrow pathologies.

SUMMARY

The present invention is based on the surprising finding that treatment with PPS showed a decrease in BMEL volume and, in some cases, complete reduction in BMELs in a patient with no post-treatment adverse events reported on follow-up. Therefore, PPS may be an improved alternative pharmaceutical option to NSAIDs and corticosteroids with potential disease modifying activity. The finding implicates the potential effectiveness of PPS as a treatment option for BMELS and joint effusion in patients and for MCs in patients. The finding also implicates the potential effectiveness of PPS as a treatment in patients who have BMELs and joint effusion and are suffering from arthritic conditions such as osteoarthritis. The finding further implicates the potential effectiveness of PPS as a treatment in patients who have MCs and are suffering from back pain such as CLBP.

According to a one aspect, there is provided a method for the treatment of bone marrow edema lesions as assessed by magnetic resonance imaging (MRI) in a mammal, the method comprising the step of administering a polysulfated polysaccharide or an acceptable salt thereof, to a mammal in need of such treatment.

According to an another aspect, there is provided a method for the treatment of Modic Endplate Changes Type I in the spine of a mammal as assessed by magnetic resonance imaging (MRI), the method comprising the step of administering a polysulfated polysaccharide or an acceptable salt thereof, to a mammal in need of such treatment.

According to another aspect, there is provided a method for the treatment of back pain in a mammal with Modic Endplate Changes Type I in the spine as assessed by magnetic resonance imaging (MRI), the method comprising the step of administering a polysulfated polysaccharide or an acceptable salt thereof, to a mammal in need of such treatment.

According to another aspect, there is provided a composition comprising a polysulfated polysaccharide or an acceptable salt thereof, and an acceptable excipient for the treatment of bone marrow edema lesions as assessed by magnetic resonance imaging (MRI) in a mammal.

According to another aspect, there is provided a composition comprising a polysulfated polysaccharide or an acceptable salt thereof, and an acceptable excipient for use in the treatment of bone marrow edema lesions as assessed by magnetic resonance imaging (MRI) in a mammal.

According to another aspect, there is provided a composition comprising a polysulfated polysaccharide or an acceptable salt thereof, and an acceptable excipient for the treatment of Modic Endplate Changes Type I in the spine of a mammal as assessed by magnetic resonance imaging (MRI).

According to another aspect, there is provided a composition comprising a polysulfated polysaccharide or an acceptable salt thereof, and an acceptable excipient for use in the treatment of Modic Endplate Changes Type I in the spine of a mammal as assessed by magnetic resonance imaging (MRI).

According to another aspect, there is provided a composition comprising a polysulfated polysaccharide or an acceptable salt thereof, and an acceptable excipient for the treatment of back pain in a mammal with Modic Endplate Changes Type I in the spine of a mammal as assessed by magnetic resonance imaging (MRI).

According to another aspect, there is provided a composition comprising a polysulfated polysaccharide or an acceptable salt thereof, and an acceptable excipient for use in the treatment of back pain in a mammal with Modic Endplate Changes Type I in the spine of a mammal as assessed by magnetic resonance imaging (MRI).

According to another aspect, there is provided use of a polysulfated polysaccharide or an acceptable salt thereof, in the treatment of bone marrow edema lesions as assessed by magnetic resonance imaging (MRI) in a mammal.

According to another aspect, there is provided use of a polysulfated polysaccharide or an acceptable salt thereof, in the manufacture of a medicament for the treatment of bone marrow edema lesions as assessed by magnetic resonance imaging (MRI) in a mammal.

According to another aspect, there is provided use of a polysulfated polysaccharide or an acceptable salt thereof, in the treatment of Modic Endplate Changes Type I in the spine of a mammal as assessed by magnetic resonance imaging (MRI).

According to another aspect, there is provided use of a polysulfated polysaccharide or an acceptable salt thereof, in the manufacture of a medicament for the treatment of Modic Endplate Changes Type I in the spine of a mammal as assessed by magnetic resonance imaging (MRI).

According to another aspect, there is provided use of a polysulfated polysaccharide or an acceptable salt thereof, in the treatment of back pain in a mammal with Modic Endplate Changes Type I in the spine as assessed by magnetic resonance imaging (MRI).

According to another aspect, there is provided use of a polysulfated polysaccharide or an acceptable salt thereof, in the manufacture of a medicament for the treatment of back pain in a mammal with Modic Endplate Changes Type I in the spine as assessed by magnetic resonance imaging (MRI).

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a cell" includes populations of a plurality of cells.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 2, from 1 to 3, from 1 to 4, from 2 to 3, from 2 to 4, from 2 to 5, from 3 to 4 etc., as well as individual and partial numbers within the recited range, for example, 1, 2, 3, 4, and 5. This applies regardless of the breadth of the disclosed range. Where specific values are required, these will be indicated in the specification.

The term "acceptable excipient" includes excipients or agents such as solvents, diluents, dispersion media, coatings, antibacterial and antifungal agents, isotonic and absorption delaying agents and the like that are physiologically compatible and are not deleterious to a compound as described herein or use thereof. The use of such carriers and agents to prepare compositions of pharmaceutically active substances is well known in the art (see, for example Remington: The Science and Practice of Pharmacy, 21st Edition; Lippincott Williams & Wilkins: Philadelphia, PA, 2005).

The term "acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of acceptable salts and their formation is known to those skilled in the art and is as described in general texts such as "Handbook of Pharmaceutical salts" P. H. Stahl, C. G. Wermuth, $1^{st}$ edition, 2002, Wiley-VCH.

The terms "administration of" and or "administering a" compound should be understood to mean providing a compound of the invention to the individual in need of treatment.

The term "composition" as used herein is intended to encompass a product comprising the specified ingredients in the specified amounts, as well as any product which results, directly or indirectly, from combination of the specified ingredients in the specified amounts.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

This invention is directed to treatments of mammal subjects. The treatment of a "mammal" subject may also be referred to the treatment of a "patient" or an "individual". A "mammal" subject has presented a clinical manifestation of a particular symptom or symptoms suggesting the need for treatment, is treated for a condition, or who has been diagnosed with a condition to be treated.

Thus, the invention is to be understood to be applicable to humans and other non-human mammals unless specifically indicated otherwise. The human can be male or female. Other non-human mammals may be a primate, livestock and farm animals (e.g. sheep, horses, cattle, pigs), domestic pets, such as cats and dogs, performance animal (e.g. racehorses, camels, greyhounds), laboratory test animal (e.g. mice, rabbits, rats, guinea pigs) as well as those mammals that usually exist in the wild but may be susceptible to treatment by virtue of such mammals being situated in zoos, wildlife parks and the like.

As used herein, the terms "treating", "treat" or "treatment" and variations thereof, refer to clinical intervention designed to alter the natural course of the subject during the course of clinical pathology. Desirable effects of treatment include decreasing the rate of disease progression, ameliorating or palliating the disease state, and remission or improved prognosis. A subject is successfully "treated", for example, if one or more of the above treatment outcomes is achieved. As used herein, the terms "treating", "treat" or "treatment" and variations thereof encompass "preventing", "prevent" or "prevention" which would be understood to refer to clinical intervention designed to avert the development of a course of clinical pathology.

An "effective amount" encompasses a "therapeutically effective" amount which refers to at least the minimum concentration or amount required to effect a measurable improvement of a particular disease (e.g., bone marrow edema). An effective amount herein may vary according to factors such as the disease state, age, sex, and weight of the patient, and the ability of the PPS to elicit a desired response in the individual. An effective amount is also one in which any toxic or detrimental effects of the PPS are outweighed by the therapeutically beneficial effects. An "effective amount" also encompasses a "prophylactically effective" amount which refers to the amount of drug or the rate of drug administration needed to produce the desired preventive result.

DESCRIPTION OF EMBODIMENTS

The present disclosure relates to a method for the treatment of bone marrow edema lesions as assessed by magnetic resonance imaging (MRI) in a mammal, the method comprising the step of administering a polysulfated polysaccharide or an acceptable salt thereof, to a mammal in need of such treatment.

Preferably, the mammal is suffering from an arthritic condition. The arthritic condition is preferably selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist. The osteoarthritis is preferably in the knee. Preferably, the osteoarthritis is in the spine (spondylosis).

The present disclosure relates to a method for the treatment of Modic Endplate Changes Type I in the spine of a mammal as assessed by magnetic resonance imaging (MRI), the method comprising the step of administering a polysulfated polysaccharide or an acceptable salt thereof, to a mammal in need of such treatment.

The present disclosure relates to a method for the treatment of back pain in a mammal with Modic Endplate Changes Type 1 in the spine as assessed by magnetic resonance imaging (MRI), the method comprising the step of administering a polysulfated polysaccharide or an acceptable salt thereof, to a mammal in need of such treatment.

Preferably, the back pain is selected from the group consisting of: general back pain, acute back pain and chronic back pain. The back pain is preferably selected from the group consisting of: general low back pain, acute low back pain and chronic low back pain. Preferably, the back pain is chronic low back pain. The Modic Endplate Changes Type I in the spine are preferably associated with Modic Endplate Changes Type II in the spine. Preferably, the Modic Endplate Changes Type I in the spine are associated with Modic Endplate Changes Type III in the spine.

The present disclosure relates to a composition comprising a polysulfated polysaccharide or an acceptable salt thereof, and an acceptable excipient for the treatment of bone marrow edema lesions as assessed by magnetic resonance imaging (MRI) in a mammal.

The present disclosure relates to a composition comprising a polysulfated polysaccharide or an acceptable salt thereof, and an acceptable excipient for use in the treatment of bone marrow edema lesions as assessed by magnetic resonance imaging (MRI) in a mammal.

Preferably, the mammal is suffering from an arthritic condition. The arthritic condition is preferably selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist. The osteoarthritis is preferably in the knee. Preferably, the osteoarthritis is in the spine (spondylosis).

The present disclosure relates to a composition comprising a polysulfated polysaccharide or an acceptable salt thereof, and an acceptable excipient for the treatment of Modic Endplate Changes Type 1 in the spine of a mammal as assessed by magnetic resonance imaging (MRI).

The present disclosure relates to a composition comprising a polysulfated polysaccharide or an acceptable salt thereof, and an acceptable excipient for use in the treatment of Modic Endplate Changes Type I in the spine of a mammal as assessed by magnetic resonance imaging (MRI).

The present disclosure relates to a composition comprising a polysulfated polysaccharide or an acceptable salt thereof, and an acceptable excipient for the treatment of back pain in a mammal with Modic Endplate Changes Type I in the spine of a mammal as assessed by magnetic resonance imaging (MRI).

The present disclosure relates to a composition comprising a polysulfated polysaccharide or an acceptable salt thereof, and an acceptable excipient for use in the treatment of back pain in a mammal with Modic Endplate Changes Type I in the spine of a mammal as assessed by magnetic resonance imaging (MRI).

Preferably, the back pain is selected from the group consisting of: general back pain, acute back pain and chronic back pain. The back pain is preferably selected from the group consisting of: general low back pain, acute low back pain and chronic low back pain. Preferably, the back pain is chronic low back pain. The Modic Endplate Changes Type I in the spine are preferably associated with Modic Endplate Changes Type II in the spine Preferably, the Modic Endplate Changes Type I in the spine are associated with Modic Endplate Changes Type III in the spine.

The present disclosure relates to use of a polysulfated polysaccharide or an acceptable salt thereof, in the treatment of bone marrow edema lesions as assessed by magnetic resonance imaging (MRI) in a mammal.

The present disclosure relates to use of a polysulfated polysaccharide or an acceptable salt thereof, in the manufacture of a medicament for the treatment of bone marrow edema lesions as assessed by magnetic resonance imaging (MRI) in a mammal.

Preferably, the mammal is suffering from an arthritic condition. The arthritic condition is preferably selected from rheumatoid arthritis or osteoarthritis. Preferably, the arthritic condition is rheumatoid arthritis. Preferably, the arthritic condition is osteoarthritis. Preferably, the osteoarthritis is in an articulating joint selected from the group consisting of: an ankle, a hip, knee, shoulder, spine and wrist. The osteoarthritis is preferably in the knee. Preferably, the osteoarthritis is in the spine (spondylosis).

The present disclosure relates to use of a polysulfated polysaccharide or an acceptable salt thereof, in the treatment of Modic Endplate Changes Type I in the spine of a mammal as assessed by magnetic resonance imaging (MRI).

The present disclosure relates to use of a polysulfated polysaccharide or an acceptable salt thereof, in the manufacture of a medicament for the treatment of Modic Endplate Changes Type I in the spine of a mammal as assessed by magnetic resonance imaging (MRI).

The present disclosure relates to use of a polysulfated polysaccharide or an acceptable salt thereof, in the treatment of back pain in a mammal with Modic Endplate Changes Type I in the spine as assessed by magnetic resonance imaging (MRI).

The present disclosure relates to use of a polysulfated polysaccharide or an acceptable salt thereof, in the manufacture of a medicament for the treatment of back pain in a mammal with Modic Endplate Changes Type I in the spine as assessed by magnetic resonance imaging (MRI).

Preferably, the back pain is selected from the group consisting of: general back pain, acute back pain and chronic back pain. The back pain is preferably selected from the group consisting of: general low back pain, acute low back pain and chronic low back pain. Preferably, the back pain is chronic low back pain. The Modic Endplate Changes Type I in the spine are preferably associated with Modic Endplate Changes Type II in the spine. Preferably, the Modic Endplate Changes Type I in the spine are associated with Modic Endplate Changes Type III in the spine.

The present disclosure also contemplates the methods, compositions and uses as described above, wherein the polysulfated polysaccharide is preferably selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octasulfate, fucoidan-1, fucoidan-2, sulfated beta-cyclodextrin, sulfated gamma-cyclodextrin and small sulfated compounds including, but are not limited to, inositol hexasulfate.

Preferably, the polysulfated polysaccharide is selected from the group consisting of high molecular weight heparin, low molecular weight heparins, pentosan polysulfate (PPS), chondroitin polysulfate and chitosan polysulfate.

The pentosan polysulfate (PPS) is preferably selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

Preferably, the pentosan polysulfate (PPS) is sodium pentosan polysulfate (NaPPS).

In one preferred embodiment, NaPPS is manufactured to the specifications lodged with the US FDA and European Community EMEA by Bene-PharmaChem GmbH & Co KG, Geretsried, Germany.

It will be recognized by persons skilled in the art, that PPS and PPS compositions suitable for administration by a variety of routes may be formulated by reference to standard textbooks in this field, such as Remington: The Science and Practice of Pharmacy, 21st Edition; Lippincott Williams & Wilkins: Philadelphia, PA, 2005). These compositions include by injection, oral (including tablets and capsules containing gastro-intestinal drug absorption extenders and enhancers), intravenous and the like.

Preferably, the treatment is by administering an injection by the intra-muscular (IM) or sub-cutaneous (SC) routes, intra-venously (IV), intra-articularly (IA), peri-articularly, topically, via suppositories or orally.

Preferably, the treatment is by administering the polysulfated polysaccharide or the acceptable salt thereof to the mammal in an effective amount of about 1 to 2 mg/kg of the mammal per dose.

Preferably, the treatment is by administering the polysulfated polysaccharide or the acceptable salt thereof to the mammal in an effective amount of about 2 mg/kg of the mammal per dose. The effective amount is preferably about 1.0 to 2.0 mg/kg of the subject per dose. In certain embodiments, the effective amount is about 1.0 to 1.5 mg/kg; 1.5 to 2.0 mg/kg; 0.5 mg/kg; 1.0 mg/kg; 1.5 mg/kg; or 2.0 mg/kg. In certain embodiments, the effective amount is a fixed dose of between about 25 mg and 4000 mg. In certain embodiments, the effective amount is a fixed dose of between about 25 mg and 300 mg. In certain embodiments, the effective amount is a fixed dose of about 25 mg, 50 mg, 75 mg, 100 mg, 125 mg, 150 mg, 175 mg, 200 mg, 225 mg, 250 mg, 275 mg, or 300 mg. In certain embodiments, the effective amount is a fixed dose of about 350 mg, 400 mg, 450 mg, 500 mg, 550 mg, 600 mg, 650 mg, 700 mg, 750 mg, 800 mg, 850 mg, 900 mg, 950 mg, 1000 mg, 2000 mg, 3000 mg, or 4000 mg.

Preferably, the treatment is by administering an injection. The treatment is preferably by administering a sub-cutaneous (SC) injection. The treatment is preferably by administering an intramuscular (IM) injection.

Preferably, administration to a human is by dosing in a treatment regimen once daily, twice weekly or thrice weekly. The administration to a human is preferably by dosing in a treatment regimen twice weekly. Preferably, the administration to a human is by dosing in a treatment regimen twice weekly with a minimum of three days and a maximum of four days between dosages. The administration to a human is preferably by dosing in a treatment regimen twice weekly for six weeks. Preferably, the total dose of polysulfated polysaccharide administered in the treatment regimen is about 200 to 4000 mg.

Thus, the dosage would be adjusted accordingly for heavier or lighter weighted individuals. The treatment regimen may be adapted according to the severity of the pain experienced by the subject. In some instances where a patient is experiencing high level pain, it is desirable to reach a therapeutic loading of the PPS as quickly as possible. This may necessitate, for example, the administration of about 1.0 mg/kg or more PPS daily until the pain is resolved.

When administration is by injection, this would normally be carried out in a clinical situation by a nurse/doctor. The person skilled in the art would understand that the key to successful treatment is to administer sufficient PPS to the subject to achieve an optimum therapeutic dose in the vicinity of the tissue lesion. Since it is known that PPS accumulates in connective tissues, loading can be achieved over time, eg daily doses of 1 mg PPS/kg over 4-5 days. It would be expected that for severe chronic cases the subject may require more than one course of treatment per year maybe twice or thrice per year.

From a safety point of view a lower dose range (1-2 mg PPS/kg or a fixed dose of about 25-50 mg) over a longer period and with decreased frequency of administration is preferred. This is because PPS is a known anticoagulant and the basal APT may be elevated with the higher dose (>3 mg PPS/kg or a fixed dose of about 150-200 mg) which could potentially encourage bleeding of any open wounds.

Whilst administration by injection is preferred, oral or topical formulations of PPS may be used as follow-up (maintenance dose) for the initial IM or SC PPS treatments. This would also be applicable to oral dosing. For administration by IV infusion, the lower doses of 0.5-1 mg PPS/kg daily are preferred.

The present disclosure also contemplates co-administration of other therapeutic agents with polysulfated polysaccharides. When other therapeutic agents are employed in combination with the compounds of the present invention they may be used for example in amounts as noted in the Physician Desk Reference (PDR) or as otherwise determined by one of ordinary skill in the art.

It will be understood, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For example, it would be understood that large animals require larger doses. For illustration, a large animal like a horse may require a fixed dose of about 4000 mg.

The determination of the suitability of the treatment of the present disclosure or in other words the diagnosis of bone marrow edema lesions (BMELs) may be established through the use of MRI. For example, as decreased signal intensity on MRI T1-weighted images and increased signal intensity on T2-weighted images. Clinical outcomes may be measured by MRI assessment of BMELs or by using patient reported outcome measurement instruments. Patient reported pain and/or functional outcomes may be used. These include the Numerical Rating Scale (NRS) for pain [33]; the Lysholm Knee Score for function [34]; Knee injury and Osteoarthritis Outcome Score (KOOS) [35] for pain, symptoms, function and quality of life; and the Oswestry Disability Index (also known as the Oswestry Low Back Pain Disability Questionnaire) for low back function [36].

Preferably, pain in the mammal is reduced after treatment. Pain in the mammal is preferably reduced as determined by the numerical rating scale (NRS).

Preferably, function in the mammal is improved after treatment. The function in the mammal is preferably improved as determined by the Lysholm Knee Score.

Preferably, the presence of bone marrow edema lesions or Modic Endplate Changes is reduced as assessed by magnetic resonance imaging. The presence of bone marrow edema lesions or Modic Endplate Changes is preferably resolved as assessed by magnetic resonance imaging.

Pre-treatment 3T proton density fat saturated images in coronal (A) and sagittal (B) planes demonstrating medial compartment bone oedema, more pronounced on the tibial side.

Axial (C) proton density fat saturated imaging at the level of suprapatellar pouch demonstrating a knee effusion.

Corresponding post treatment 3T proton density fat saturated images in coronal (D) and sagittal (E) planes demonstrating resolution of medial compartment bone oedema. Axial (F) proton density fat saturated imaging at the level of suprapatellar pouch demonstrating reduction in size of knee effusion.

Figure 2:
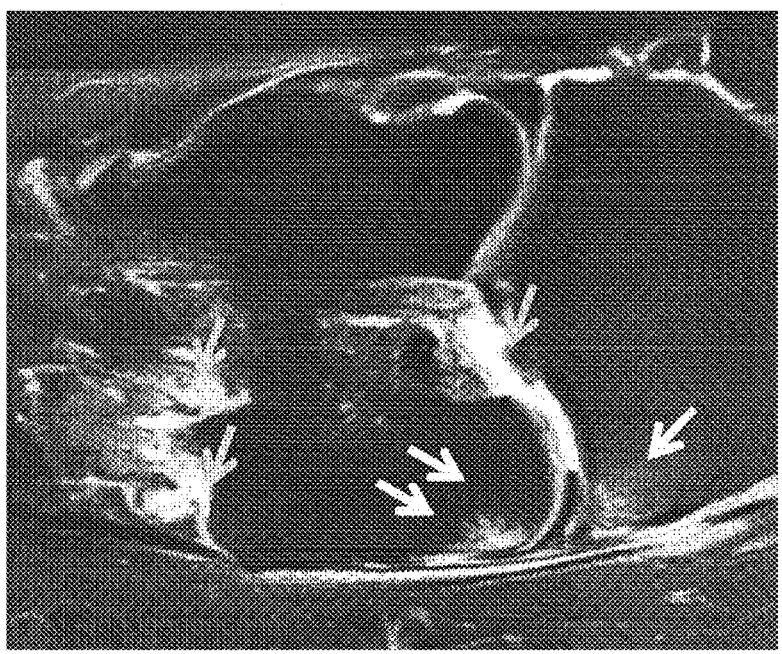
Figure 2:
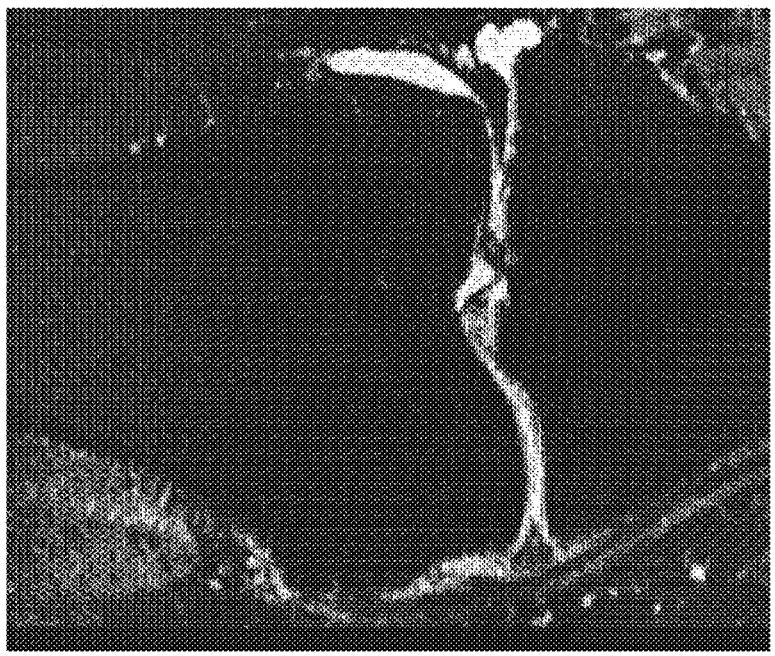

FIG. 2. Particular MRI images from case history of Example 2.
  A: Before PPS MRI showing BME Lesions (arrows) effusions in joint space (arrows); High NRS Pain Score=8; Lysholm Score: 37 (Poor knee function).
  B: Post-PPS treatment MRI Showing complete resolution of BME lesions and effusions; Pain NRS=0 (pain resolved); Lysholm Score: 65 (Fair knee function)

EXAMPLE EMBODIMENTS

1. A method for the treatment of bone marrow edema lesions as assessed by magnetic resonance imaging (MRI) in a mammal, the method comprising the step of administering a polysulfated polysaccharide or an acceptable salt thereof, to a mammal in need of such treatment.
2. The method according to example embodiment 1, wherein the mammal is suffering from osteoarthritis.
3. The method according to example embodiment 2, wherein the osteoarthritis is in an articulating joint selected from the group consisting of: an ankle, a hip, knee, shoulder, spine and wrist.
4. The method according to example embodiment 3, wherein the osteoarthritis is in the knee.
5. The method according to example embodiment 3, wherein the osteoarthritis is in the spine (spondylosis).
6. A method for the treatment of Modic Endplate Changes Type I in the spine of a mammal as assessed by magnetic resonance imaging (MRI), the method comprising the step of administering a polysulfated polysaccharide or an acceptable salt thereof, to a mammal in need of such treatment.
7. A method for the treatment of back pain in a mammal with Modic Endplate Changes Type I in the spine as assessed by magnetic resonance imaging (MRI), the method comprising the step of administering a polysulfated polysaccharide or an acceptable salt thereof, to a mammal in need of such treatment.
8. The method according to example embodiment 7, wherein the back pain is selected from the group consisting of: general back pain, acute back pain and chronic back pain.
9. The method according to example embodiment 8, wherein the back pain is selected from the group consisting of: general low back pain, acute low back pain and chronic low back pain.
10. The method according to example embodiment 9, wherein the back pain is chronic low back pain.
11. The method according to any one of example embodiments 6 to 10, wherein the Modic Endplate Changes Type I in the spine are associated with Modic Endplate Changes Type II in the spine.
12. The method according to any one of example embodiments 6 to 10, wherein the Modic Endplate Changes Type I in the spine are associated with Modic Endplate Changes Type III in the spine.
13. A composition comprising a polysulfated polysaccharide or an acceptable salt thereof, and an acceptable excipient for the treatment of bone marrow edema lesions as assessed by magnetic resonance imaging (MRI) in a mammal.
14. A composition comprising a polysulfated polysaccharide or an acceptable salt thereof, and an acceptable excipient for use in the treatment of bone marrow edema lesions as assessed by magnetic resonance imaging (MRI) in a mammal.
15. The composition according to example embodiment 13 or example embodiment 14, wherein the mammal is suffering from osteoarthritis.
16. The composition according to example embodiment 15, wherein the osteoarthritis is in an articulating joint selected from the group consisting of: an ankle, a hip, knee, shoulder, spine and wrist.
17. The composition according to example embodiment 16, wherein the osteoarthritis is in the knee.
18. The composition according to example embodiment 16, wherein the osteoarthritis is in the spine (spondylosis).
19. A composition comprising a polysulfated polysaccharide or an acceptable salt thereof, and an acceptable excipient for the treatment of Modic Endplate Changes Type I in the spine of a mammal as assessed by magnetic resonance imaging (MRI).
20. A composition comprising a polysulfated polysaccharide or an acceptable salt thereof, and an acceptable excipient for use in the treatment of Modic Endplate Changes Type I in the spine of a mammal as assessed by magnetic resonance imaging (MRI).
21. A composition comprising a polysulfated polysaccharide or an acceptable salt thereof, and an acceptable excipient for the treatment of back pain in a mammal with Modic Endplate Changes Type I in the spine of a mammal as assessed by magnetic resonance imaging (MRI).
22. A composition comprising a polysulfated polysaccharide or an acceptable salt thereof, and an acceptable excipient for use in the treatment of back pain in a mammal with Modic Endplate Changes Type I in the spine of a mammal as assessed by magnetic resonance imaging (MRI).
23. The composition according to example embodiment 21 or example embodiment 22, wherein the back pain mammal is selected from the group consisting of: general back pain, acute back pain and chronic back pain.
24. The composition according to example embodiment 23, wherein the back pain is selected from the group consisting of: general low back pain, acute low back pain and chronic low back pain.
25. The composition according to example embodiment 24, wherein the back pain is chronic low back pain.
26. The composition according to any one of example embodiments 19 to 25, wherein the Modic Endplate Changes Type I in the spine are associated with Modic Endplate Changes Type II in the spine.

27. The composition according to any one of example embodiments 19 to 25, wherein the Modic Endplate Changes Type I in the spine are associated with Modic Endplate Changes Type III in the spine.
28. Use of a poly sulfated polysaccharide or an acceptable salt thereof, in the treatment of bone marrow edema lesions as assessed by magnetic resonance imaging (MT) in a mammal.
29. Use of a polysulfated polysaccharide or an acceptable salt thereof, in the manufacture of a medicament for the treatment of bone marrow edema lesions as assessed by magnetic resonance imaging (MRI) in a mammal.
30. The use according to example embodiment 28 or example embodiment 29, wherein the mammal is suffering from osteoarthritis.
31. The use according to example embodiment 30, wherein the osteoarthritis is in an articulating joint selected from the group consisting of: an ankle, a hip, knee, shoulder, spine and wrist.
32. The use according to example embodiment 31, wherein the osteoarthritis is in the knee.
33. The use according to example embodiment 31, wherein the osteoarthritis is in the spine (spondylosis).
34. Use of a polysulfated polysaccharide or an acceptable salt thereof, in the treatment of Modic Endplate Changes Type I in the spine of a mammal as assessed by magnetic resonance imaging (MRI).
35. Use of a polysulfated polysaccharide or an acceptable salt thereof, in the manufacture of a medicament for the treatment of Modic Endplate Changes Type I in the spine of a mammal as assessed by magnetic resonance imaging (MRI).
36. Use of a polysulfated polysaccharide or an acceptable salt thereof, in the treatment of back pain in a mammal with Modic Endplate Changes Type I in the spine as assessed by magnetic resonance imaging (MRI).
37. Use of a polysulfated polysaccharide or an acceptable salt thereof, in the manufacture of a medicament for the treatment of back pain in a mammal with Modic Endplate Changes Type I in the spine as assessed by magnetic resonance imaging (MRI).
38. The use according to example embodiment 36 or example embodiment 37, wherein the back pain is selected from the group consisting of: general back pain, acute back pain and chronic back pain.
39. The use according to example embodiment 38, wherein the back pain is selected from the group consisting of: general low back pain, acute low back pain and chronic low back pain.
40. The use according to example embodiment 39, wherein the back pain is chronic low back pain.
41. The use according to any one of example embodiments 34 to 40, wherein the Modic Endplate Changes Type I in the spine are associated with Modic Endplate Changes Type II in the spine.
42. The use according to any one of example embodiments 34 to 40, wherein the Modic Endplate Changes Type I in the spine are associated with Modic Endplate Changes Type III in the spine.
43. A method according to any one of example embodiments 1 to 12, a composition according to any one of example embodiments 13 to 27 or a use according to any one of example embodiments 28 to 42, wherein the polysulfated polysaccharide is selected from the group consisting of high molecular weight heparin, low molecular weight heparins, the heparan sulfates, pentosan polysulfate, chondroitin polysulfate, chitosan polysulfate, dermatan polysulfate sulodexide, dextran sulfate, polysulfated inulin, sulfated lactobionic acid amide, sulfated bis-aldonic acid amide, sucrose octa-sulfate, fucoidan-1, fucoidan-2, sulfated beta-cyclodextrin, sulfated gamma-cyclodextrin and small sulfated compounds including, but are not limited to, inositol hexasulfate.
44. The method, the composition or the use according to example embodiment 43, wherein the polysulfated polysaccharide is selected from the group consisting of high molecular weight heparin, low molecular weight heparins, pentosan polysulfate (PPS), chondroitin polysulfate and chitosan polysulfate.
45. The method, the composition or the use according to example embodiment 44, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).
46. The method, the composition or the use according to example embodiment 45, wherein the pentosane polysulfate (PPS) is sodium pentosan polysulfate (NaPPS).
47. The method, the composition or the use according to any one of example embodiments 1 to 46, wherein treatment is by administering an injection by the intramuscular (IM) or sub-cutaneous (SC) routes, intravenously (IV), intra-articularly (IA), peri-articularly, topically, via suppositories or orally.
48. The method, the composition or the use according to any one of example embodiments 1 to 47, wherein treatment is by administering the polysulfated polysaccharide or the acceptable salt thereof to the mammal in an effective amount of about 1 to 2 mg/kg of the mammal per dose or an effective amount of about 25 mg, 50 mg, 75 mg, 100 mg, 125 mg, 150 mg, 175 mg, 200 mg, 225 mg, 250 mg, 275 mg, or 300 mg as a fixed dose.
49. The method, the composition or the use according to any one of example embodiments 1 to 48, wherein the treatment is by administering the polysulfated polysaccharide or the acceptable salt thereof to the mammal in an effective amount of about 2 mg/kg of the mammal per dose.
50. The method, the composition or the use according to any one of example embodiments 47 to 49, wherein the treatment is by administering an injection.
51. The method, the composition or the use according to example embodiment 50, wherein the treatment is by administering a sub-cutaneous (SC) injection.
52. The method, the composition or the use according to any one of example embodiments 47 to 51, wherein administration to a human is by dosing in a treatment regimen once daily, twice weekly or thrice weekly.
53. The method, the composition or the use according to example embodiment 52, wherein administration to a human is by dosing in a treatment regimen twice weekly.
54. The method, the composition or the use according to example embodiment 53, wherein administration to a human is by dosing in a treatment regimen twice weekly with a minimum of three days and a maximum of four days between dosages.
55. The method, the composition or the use according to example embodiment 54, wherein administration to a human is by dosing in a treatment regimen twice weekly for six weeks.

56. The method, the composition or the use according to example embodiment 55, wherein the total dose of polysulfated polysaccharide administered in the treatment regimen is about 200 to 4000 mg.
57. The method, the composition or the use according to any one of example embodiments 1 to 56, wherein pain in the mammal is reduced after treatment.
58. The method, the composition or the use according to example embodiment 57, wherein pain in the mammal is reduced as determined by the numerical rating scale (NRS).
59. The method, the composition or the use according to any one of example embodiments 1 to 58, wherein function in the mammal is improved after treatment.
60. The method, the composition or the use according to example embodiment 59, wherein the function in the mammal is improved as determined by the Lysholm Knee Score described herein.
61. The method, the composition or the use according to any one of example embodiments 1 to 60, wherein the presence of bone marrow edema lesions or Modic Endplate Changes is reduced as assessed by magnetic resonance imaging.
62. The method, the composition or the use according to any one of example embodiments 1 to 60, wherein the presence of bone marrow edema lesions or Modic Endplate Changes is resolved as assessed by magnetic resonance imaging.

EXAMPLES

Example 1—Effects of Pentosan on Clinical Outcomes of Pain and Function in Knee OA Patients (n=35) with Bone Marrow Edema Lesions on MRI Example 1 is a study of the safety, tolerability and results of patients treated with PPS with Bone Marrow Edema Lesions of the knee and suffering from osteoarthritis under the TGA Special Access Scheme (B). (Approval to use PPS as treatment for the patient was acquired from Department of Health-Therapeutic Goods Administration, Australian Government under the Special Access Scheme (SAS) since the injectable form of PPS was not a registered product in Australia.)

Patients in the study had the following characteristics:
High pain scores
Poor joint function scores
MRI evidence of Bone Marrow Edema Lesions and joint effusions
Kellgren-Lawrence (3-4) OA subjects currently on waiting list for Total Knee Replacement
Failed standard of care including intraarticular injections of corticosteroids
The protocol featured the following:
Treatment: 2× weekly intramuscular injections of 2 mg/kg for 3 weeks (total of 6 injections)
All patients abstained from NSAIDs during PPS treatment
The treatment outcomes of pain and function were scored before and after PPS treatment 2 to 4 weeks after the last PPS injection
All patients had baseline subchondral BML.
The clinical outcomes including BMEL assessment, and pain and functional outcome scores are displayed in Table 1.

TABLE 1

Clinical outcomes

| Patient Initials | Before PPS/ BMEL | After PPS/ BMEL | Before PPS/ NRS Pain | After PPS/ NRS Pain | Before PPS/ Lysholm Knee Score | After PPS/ Lysholm Knee Score |
|---|---|---|---|---|---|---|
| SM 60 yo, M | Severe (>20 mm) | Moderate (5 mm to 20 mm) | 4 | 0 | 54 | 73 |
| PA 70 yo, M | Moderate (5 mm to 20 mm) | Minimal (<5 mm) | 4 | 1 | 73 | 90 |
| KO 70 yo, F | Moderate (5 mm to 20 mm) | Absent | 8 | 0 | 37 | 70 |

Legend

Numerical Rating Scale (NRS) [33] is an 11-point scale (0-10). A state of no pain is 0 and the worst pain imaginable is 10.

Lysholm Knee Score [34] is a total score of 0-100 is calculated based on the results from the eight functional components of the Lysholm knee score scale: Limp (5 points), Support (5 points), Locking (15 points), Instability (25 points), Pain (25 points), Swelling (10 points), Stair climbing (10 points), and Squatting (5 points). The total score is assigned to rating categories as follows: 95-100 indicates excellent, 84-94 indicates good, 65-83 indicates fair and <65 indicates poor function.

In conclusion, no adverse events were reported with the use of PPS under the TGA SAS(B) in patients with Bone Marrow Edema Lesions and suffering from osteoarthritis. Standard four week course of PPS resulted in a clearly visible BMEL reduction and improved pain and mobility scores.

In further work, a dosing and treatment regimen of 2 mg/kg PPS or a fixed dose of 150 mg administered by slow SC injection twice-weekly for 6 weeks surprisingly gave consistent BMEL volume reduction and, in some cases, complete reduction of the BMEL as assessed by magnetic resonance imaging.

Example 2—Case Report of Knee Osteoarthritis

Summary

Example 2 details the case of a 70-year-old female with knee osteoarthritis presenting with a high level of knee pain, scoring 8 on the Numerical Rating Scale-(NRS) and functional limitation demonstrating a poor Lysholm Knee Score of 37. MRI scans of the knee revealed subchondral bone marrow edema lesions (BML) in the medial femoral condyle and medial tibial plateau. The patient was administered a course of Pentosan Polysulphate Sodium (PPS) intramuscularly twice weekly for 3 weeks. MRI scans two weeks post-treatment showed complete resolution of the bone marrow oedema at the medial femoral condyle and medial tibial plateau with concomitant recovery from pain (NRS pain score of 0) and a 43% improvement of the Lysholm Knee score. In addition, marked reduction in joint effusion was also demonstrated in the MRI scan post PPS therapy. These MRI interpretations corroborate improved clinical outcome measures ensuing therapeutic intervention with PPS.

Case History

A 70-year-old female with a history of arthroscopic partial medial meniscectomy presented with pain of the left knee and was on a waiting list for total knee replacement. The patient had failed to respond to intra-articular Cortisol administration at the time of arthroscopy. The MRI scan of the knee, using a 3-Tesla proton density turbo spin echo fat saturated acquisition with TR 3000 ms TE 30 ms, demonstrated subchondral BML associated with focal full thickness chondral defects at the medial aspects of the weight bearing medial femoral condyle and medial tibial plateau. The BML in the medial femoral condyle measured 11×7×12 mm (CC×transverse×AP) and the medial tibial plateau BML measured 8×8×8 mm (CC×transverse×AP). In addition, the axial proton density fat saturated imaging at the level of suprapatellar pouch revealed a knee effusion and a recurrent tear of the medial meniscus (body and posterior horn). Following patient consent, the pain assessment score was determined by the Numerical Rating Scale (NRS) [33] and functional capacity assessments included the Lysholm knee score [34]. At pre-treatment, the NRS pain score was severe with a score of 8 out of 10 (range 0-10) and the Lysholm Knee score was 37 out of 100 reflecting poor knee function indicated by problems in stair climbing and limping.

Since PPS is a weak anticoagulant with 1/15 the activity of heparin, the patient was monitored for safety by assessments of complete blood count, APTT, prothrombin time, liver function tests, renal function tests and serum calcium prior to commencement of treatment and periodically during treatment with Pentosan Polysulphate Sodium. The clinical status of the patient was checked regularly throughout the course of the treatment and follow up period.

After evaluation, the patient was considered suitable for treatment with Pentosan Polysulphate Sodium (PPS) under the SAS. The patient was administered 2 mg/kg of PPS twice weekly with a minimum of three and a maximum of four days between dosages. Six intramuscular injections were administered into the gluteus maximus muscle over a three-week period (2 injections per week). Three follow-up appointments were made at 10, 24 and 38 days post-completion of injection regimen. Five weeks after the first PPS injection, MRI scans were performed using a 3-Tesla proton density fat saturated SPACE acquisition with TR 1200 ms TE 28 ms which demonstrated complete resolution of the bone marrow oedema lesions at the medial femoral condyle and medial tibial plateau. In addition, the axial imaging at the level of the suprapatellar pouch demonstrated reduction in the size of the knee effusion. The patient displayed a marked functional improvement of 43% in the Lysholm Knee score at four weeks after the last injection with a score of 65 and a robust recovery from pain as annotated by the NRS pain score of 0. During PPS treatment and the follow up period the patient did not present with any drug-related or nondrug-related adverse response.

Discussion and Conclusion

Figure 1:
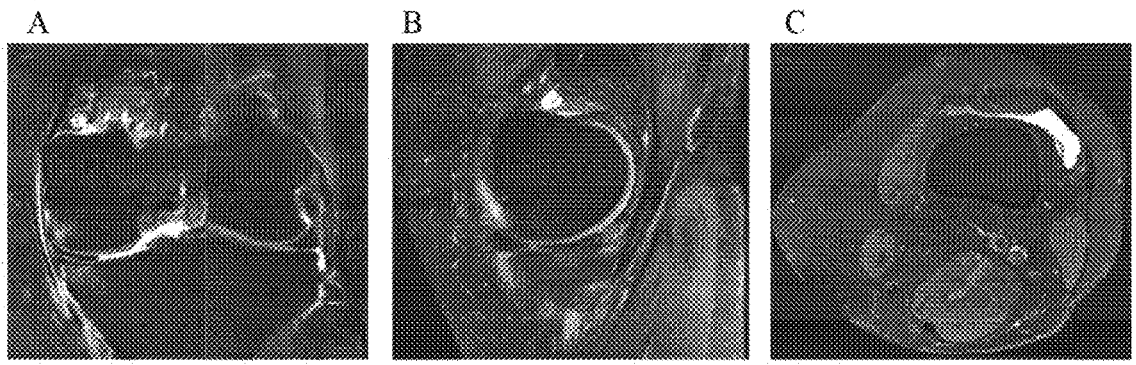
FIG. 1. MRI images from patient study of Example 1.
Figure 1:
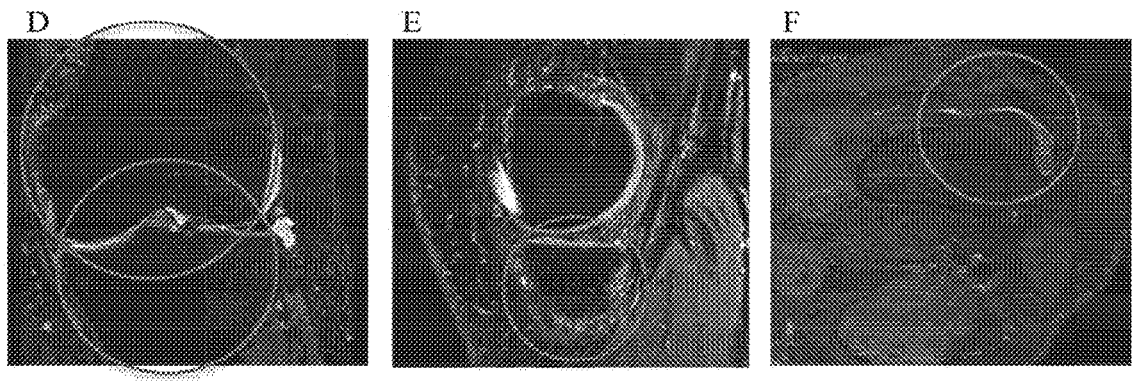

The MRT findings performed using a 3-Tesla proton density fat saturated SPACE acquisition with TR 1200 ms TE 28 ms demonstrated that a course of intramuscular PPS produced complete resolution of the BML at the medial femoral condyle and medial tibial plateau (see FIG. 1 and FIG. 2). In addition, the axial imaging at the level of the suprapatellar pouch demonstrated reduction in the size of the knee effusion. In addition, the patient did not report any adverse effects due to PPS administration.

In conclusion, treatment by PPS showed complete reduction in BMELs with no post-treatment adverse events reported on follow-up with the patient. Results from this case report implicate the potential effectiveness of PPS as a treatment option for BMELs and and joint effusion, and also implicate the potential effectiveness of PPS as a treatment option for BMELs and joint effusion in patients suffering from arthritic conditions such as osteoarthritis.

Example 3—Case Report for Chronic Low Back Pain

Patient GW, a 52 year-old male with chronic lower back pain with a Modic Type 1 pattern on MRI scan of the L3/L4 and L4 L5 region of the spine presented in the clinics with unresolved persistent pain despite current standard of care treatment with Mobic, an NSAID.

The baseline NRS pain score prior to treatment with PPS was a high score of 7. Patient was administered by subcutaneous injection a dose of 150 mg fixed dose of PPS twice weekly for 4 weeks (ie a total of 8 injections). The patient experienced improvement in pain soon after the 4$^{th}$ injection and after the 8$^{th}$ injection (completion of treatment) experienced a significant reduction in pain recording a low NRS pain score of 2 to 3. During the course of the treatment the patient had abstained from any other therapeutic intervention. No adverse events were experienced during and after the course of PPS treatment.

In further work, a dosing and treatment regimen of 2 mg/kg PPS or a fixed dose of 150 mg administered by slow SC injection twice-weekly for 6 weeks surprisingly gave consistent resolution of Modic Changes as assessed by magnetic resonance imaging.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

1. Davies-Tuck M L, Wluka A E, Wang Y, English D R, Giles G G, Cicuttini F. The natural history of bone marrow lesions in community-based adults with no clinical knee osteoarthritis. Annals of the Rheumatic Diseases. 2009; 68(6):904-8.
2. Felson D T, Chaisson C E, Hill C L, Totterman S M, Gale M E, Skinner K M, et al. The association of bone marrow lesions with pain in knee osteoarthritis. Annals of internal medicine. 2001; 134(7):541-9.
3. Zhai G, Blizzard L, Srikanth V, Ding C, Cooley H, Cicuttini F, et al. Correlates of knee pain in older adults: Tasmanian Older Adult Cohort Study. Arthritis and rheumatism. 2006; 55(2):264-71.
4. Roemer F W, Guermazi A, Javaid M K, Lynch J A, Niu J, Zhang Y, et al. Change in MRI-detected subchondral bone marrow lesions is associated with cartilage loss: the MOST Study. A longitudinal multicentre study of knee osteoarthritis. Ann Rheum Dis. 2009; 68(9): 1461-5.
5. Hunter D J, Zhang Y, Niu J, Goggins J, Amin S, LaValley M P, et al. Increase in bone marrow lesions associated with cartilage loss: a longitudinal magnetic resonance imaging study of knee osteoarthritis. Arthritis and rheumatism. 2006; 54(5): 1529-35.
6. Wluka A E, Wang Y, Davies-Tuck M, English D R, Giles G G, Cicuttini F M. Bone marrow lesions predict progression of cartilage defects and loss of cartilage volume in healthy middle-aged adults without knee pain over 2 yrs. Rheumatology (Oxford, England). 2008; 47(9): 1392-6.
7. Wluka A E, Hanna F, Davies-Tuck M, Wang Y, Bell R J, Davis S R, et al. Bone marrow lesions predict increase in knee cartilage defects and loss of cartilage volume in middle-aged women without knee pain over 2 years. Ann Rheum Dis. 2009; 68(6):850-5.
8. Starr A M, Wessely M A, Albastaki U, Pierre-Jerome C, Kettner N W. Bone marrow edema: pathophysiology, differential diagnosis, and imaging. Acta radiologica (Stockholm, Sweden: 1987). 2008; 49(7):771-86.
9. Altahawi F F, Blount K J, Morley N P, Raithel E, Omar I M. Comparing an accelerated 3D fast spin-echo sequence (CS-SPACE) for knee 3-T magnetic resonance imaging with traditional 3D fast spin-echo (SPACE) and routine 2D sequences. Skeletal radiology. 2017; 46(1):7-15.
10. Felson D T, McLaughlin S, Goggins J, LaValley M P, Gale M E, Totterman S, et al. Bone marrow edema and its relation to progression of knee osteoarthritis. Annals of internal medicine. 2003; 139(5 Pt I): 330-6.
11. Raynauld J P, Martel-Pelletier J, Berthiaume M J, Abram F, Choquette D, Haraoui B, et al. Correlation between bone lesion changes and cartilage volume loss in patients with osteoarthritis of the knee as assessed by quantitative magnetic resonance imaging over a 24-month period. Ann Rheum Dis. 2008; 67(5):683-8.
12. Tanamas S K, Wluka A E, Pelletier J P, Pelletier J M, Abram F, Berry P A, et al. Bone marrow lesions in people with knee osteoarthritis predict progression of disease and joint replacement: a longitudinal study. Rheumatology (Oxford, England). 2010; 49(12):2413-9.
13. Lowitz T, Museyko O, Bousson V, Laouisset L, Kalender W A, Laredo I D, et al. Bone marrow lesions identified by MRI in knee osteoarthritis are associated with locally increased bone mineral density measured by QCT. Osteoarthritis and cartilage. 2013; 21(7):957-64.
14. Laslett L L, Dore D A, Quinn S J, Boon P, Ryan E, Winzenberg T M, et al. Zoledronic acid reduces knee pain and bone marrow lesions over 1 year: a randomised controlled trial. Ann Rheum Dis. 2012; 71(8): 1322-8.
15. Varenna M, Zucchi F, Failoni S, Becciolini A, Berruto M. Intravenous neridronate in the treatment of acute painful knee osteoarthritis: a randomized controlled study. Rheumatology (Oxford, England). 2015; 54(10): 1826-32.
15A. Rahme R, Moussa R. The modic vertebral endplate and marrow changes: pathologic significance and relation to low back pain and segmental instability of the lumbar spine. AJNR Am I Neuroradiol. 2008 May; 29(5):838-42.
16. Scully M F, Weerasinghe K M, Ellis V, Djazaeri B, Kakkar V V. Anticoagulant and antiheparin activities of a pentosan polysulphate. Thrombosis Research 1983; 31(1) 87-97.
17. Krupinski K, Breddin U K, Casu B. Anticoagulant and antithrombotic effects of chemically modified heparins and pentosan polysulfate. Haemostasis 1990; 20(2):81-92.
18. Shanmugam M, Mody K H. Heparinoid-active sulphated polysaccharides from marine algae as potential blood anticoagulant agents. Current Science 2000; 79(12): 1672-1683.
19. Vongchan P, Sajomsang W, Kasinrerk W, Subyen D, Kongrawelert P. Anticoagulant activities of the chitosan polysulfate synthesized from marine crab shell by semi-heterogeneous conditions. Science Asia 2003; 29: 115-120.
20. Vinazzer H. Prevention of recurrence of cerebrovascular thromboses. A randomized comparative study acetylsalicylic acid and sodium pentosan polysulfate. Fortschr Med 1987; 105(5):79-85.
21. Losonczy H, David M, Nagy I. Effect of pentosan polysulfate on activated partial thromboplastin time, thrombin time, euglobulin clot lysis and tissue-type plasminogen activator and plasminogen activator inhibitor activities in patients with thromboembolic disease. Semin Thromb Hemost 1991; 17(4):394-8.
22. Anderson V R, Perry C M. Pentosan polysulfate: a review of its use in the relief of bladder pain or discomfort in interstitial cystitis. Drugs 2006; 66(6):821-35.
23. Dimitrakov J, Kroenke K, Steers W D, Berde C, Zurakowski D, Freeman M R, Jackson J L. Pharmacologic management of painful bladder syndrome/interstitial cystitis: a systematic review. Arch Intern Med 2007; 167(18): 1922-9.
24. Davis E L, El Khoudary S R, Talbott E O, Davis J, Regan L R. Safety and efficacy of the use of intravesical and oral pentosan polysulfate sodium for interstitial cystitis: a randomized double-blind clinical trial. J Urol 2008; 179 (1): 177-85.
25. WO 2008/144836. Sulphated xylans for treatment or prophylaxis of respiratory diseases.
26. WO 2002/41901. Treatment of osteoporosis.
27. WO 2012/103588. Treatment of bone marrow (oedema) with polysulfated polysaccharides.
28. Mayerhoefer M E, Krmaer J, Breitenseher M J, Norden C, Vakil-Adli A, Hofmann S et al. Short-term outcome of painful bone marrow oedema of the knee following oral treatment with iloprost or tramadol: results of an exploratory phase 11 study of 41 patients. Rheumatology. 2007; 46(9): 1460-5.
29. Batemen D, Kennedy J. Non-steroidal anti-inflammatory drugs and elderly patients. British Medical Journal. 1995; 310:817-8.
30. Brandt K D. Should nonsteroidal anti-inflammatory drugs be used to treat osteoarthritis? Rheumatic diseases clinics of North America. 1993; 19(1):29-44.
31. O'Mahony D. Prevention of corticosteroid-induced osteoporosis and fractures. Journal of Clinical Pharmacy and Therapeutics. 1999; 24(2):83-5.
32. Miyata N, Kumagai K, Osaki M, Murata M, Tomita M, Hozumi A, et al. Pentosan reduces osteonecrosis of femoral head in SHRSP. Clinical and experimental hypertension (New York, NY: 1993). 2010; 32(8):511-6.
33. Hjermstad M J, Fayers P M, Haugen D F, Caraceni A, Hanks G W, Loge J H, etal. Studies comparing Numerical Rating Scales, Verbal Rating Scales, and Visual Analogue Scales for assessment of pain intensity in adults: a systematic literature review. Journal of pain and symptom management. 2011; 41(6): 1073-93.
34. Briggs K K, Kocher M S, Rodkey W G, Steadman J R. Reliability, validity, and responsiveness of the Lysholm knee score and Tegner activity scale for patients with meniscal injury of the knee. The Journal of bone and joint surgery American volume. 2006; 88(4):698-705.
35. Ross E M, Lohmander L S. Knee injury and Osteoarthritis Outcome Score (KOOS): from joint injury to osteoarthritis. Health Qual Life Outcomes 2003; 1:64.
36. Fairbank J C T and Pynsent P B (2000) The Owestery Disability Index. Spine, 25(22):2940-2953.

The invention claimed is:

1. A method for improving knee function and reducing knee pain in a human having osteoarthritis 3-4 on the Kellgren-Lawrence scale in a knee and experiencing pain of at least 8 on the NRS scale, the method including determining that treatment of the knee with a corticosteroid has failed to improve knee function and reduce pain and administering intramuscularly an amount of an acceptable salt of pentosan polysulfate, to the human in need of such treatment, in a manner so as to improve knee function by about 23% to about 89% as determined by Lysholm Knee Score.

2. The method according to claim 1, wherein the pentosan polysulfate (PPS) is selected from the group consisting of: the sodium salt of pentosan polysulfate (NaPPS), the magnesium salt of pentosan polysulfate (MgPPS), the calcium salt of pentosan polysulfate (CaPPS), and the zinc salt of pentosan polysulfate (ZnPPS).

3. The method according to claim 2, wherein the pentosan polysulfate (PPS) is sodium pentosan polysulfate (NaPPS).

4. The method according to claim 3, wherein the treatment is by administering the sodium pentosan polysulfate or the acceptable salt thereof to the human in an effective amount of about 1 to 2 mg/kg of the human per dose or an effective amount of between about 25 mg and 300 mg as a fixed dose.

5. The method according to claim 3, wherein the treatment is by administering the sodium pentosan polysulfate or the acceptable salt thereof to the human in an effective amount of about 2 mg/kg of the human per dose or an effective amount of about 150 mg as a fixed dose.

6. The method according to claim 3, wherein administration is by dosing in a treatment regimen once daily, twice weekly or thrice weekly.

7. The method according to claim 6, wherein administration is by dosing in a treatment regimen twice weekly.

8. The method according to claim 7, wherein administration is by dosing in a treatment regimen twice weekly with a minimum of three days and a maximum of four days between dosages.

9. The method according to claim 8, wherein administration is by dosing in a treatment regimen twice weekly for six weeks.

10. The method according to claim 9, wherein the total dose of the sodium pentosan polysulfate or the acceptable salt thereof administered in the treatment regimen is about 200 to 4000 mg.

11. The method according to claim 1, wherein the function of the knee is improved by about 23% to about 35%.

12. The method according to claim 1, wherein the function of the knee is improved by about 23 to about 43%.

13. The method according to claim 1, wherein the function of the knee is improved about 89%.

* * * * *